United States Patent [19]

Hickham et al.

[11] Patent Number: 4,718,848

[45] Date of Patent: Jan. 12, 1988

[54] ORTHODONTIC HEADGEAR AND A METHOD FOR PREVENTING INJURIES TO PATIENTS UNDERGOING ORTHODONTIC TREATMENT WITH AN ORTHODONTIC HEADGEAR

[76] Inventors: John H. Hickham; David A. Hickham, both of 326 23rd St., Kenner, La. 70062

[21] Appl. No.: 856,282

[22] Filed: Apr. 28, 1986

[51] Int. Cl.⁴ .............................................. A61C 7/00
[52] U.S. Cl. ...................................................... 433/5
[58] Field of Search ........................................ 433/5, 6

[56] References Cited

U.S. PATENT DOCUMENTS 4,226,589 10/1980 Klein ........................................ 433/5
4,402,669 9/1983 Frazier ..................................... 433/5

Primary Examiner—Robert Peshock
Attorney, Agent, or Firm—John Wade Carpenter

[57] ABSTRACT

An orthodontic headgear for preventing injuries to patients undergoing orthodontic treatment having an inner orthodontic bow adapted to be secured to braces and an outer orthodontic bow integrally bound to the inner orthodontic bow and formed with a pair of arms terminating into a pair of arm ends. A pair of safety hooks is connected removably to the pair of arm ends respectively. A safety line is bound to each of the pair of safety hooks. A method for preventing injuries to patients undergoing orthodontic treatment with the orthodontic headgear comprising binding the pair of safety hooks to the ends of the safety line; and securing removably respectively to the pair of arm ends the pair of safety hooks in order to limit the distance the outer bow and the inner bow can be displaced forward to prevent the ends of the inner bow from possibly puncturing the eyes of the patient, or other injuries.

5 Claims, 11 Drawing Figures

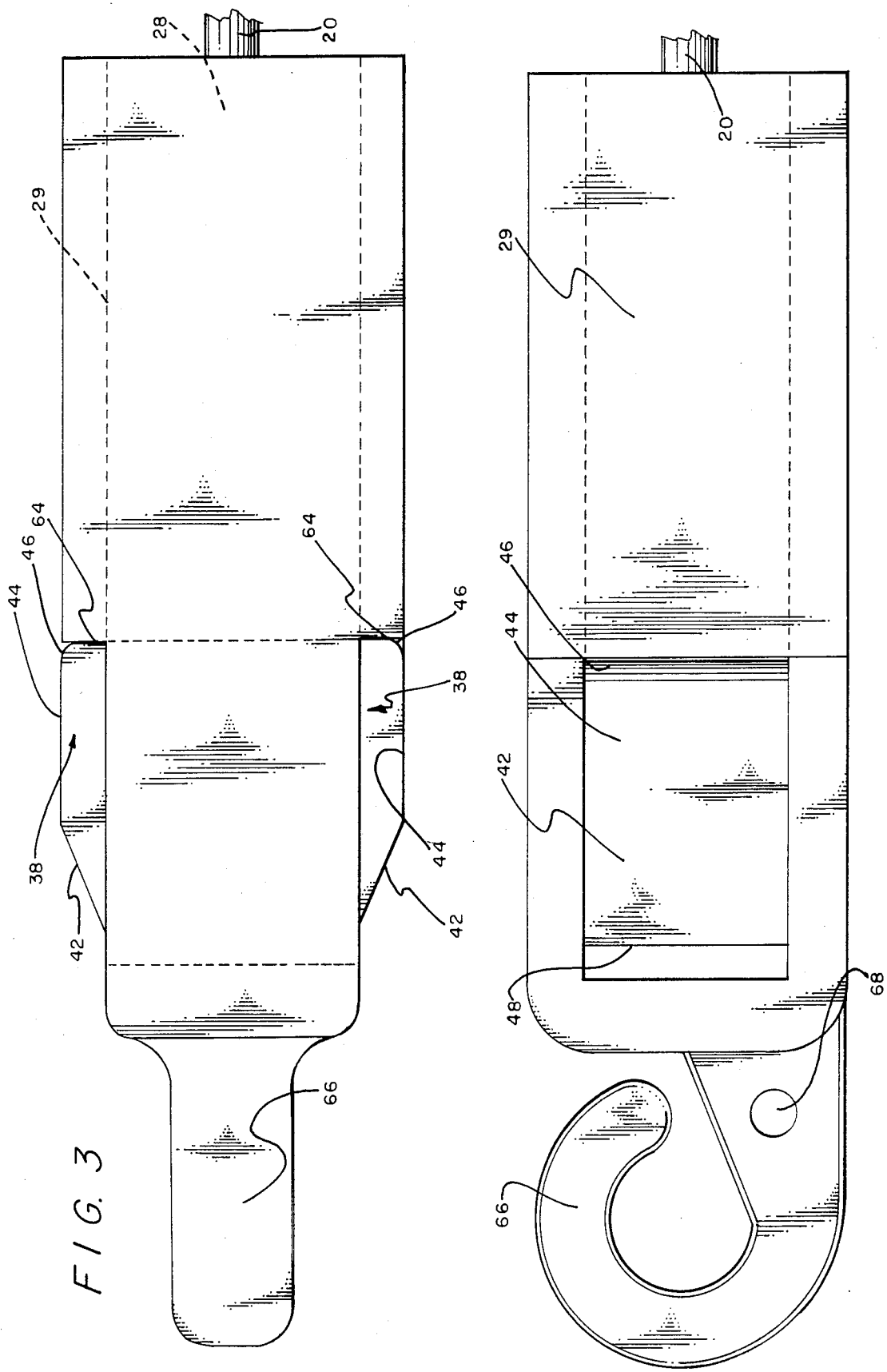

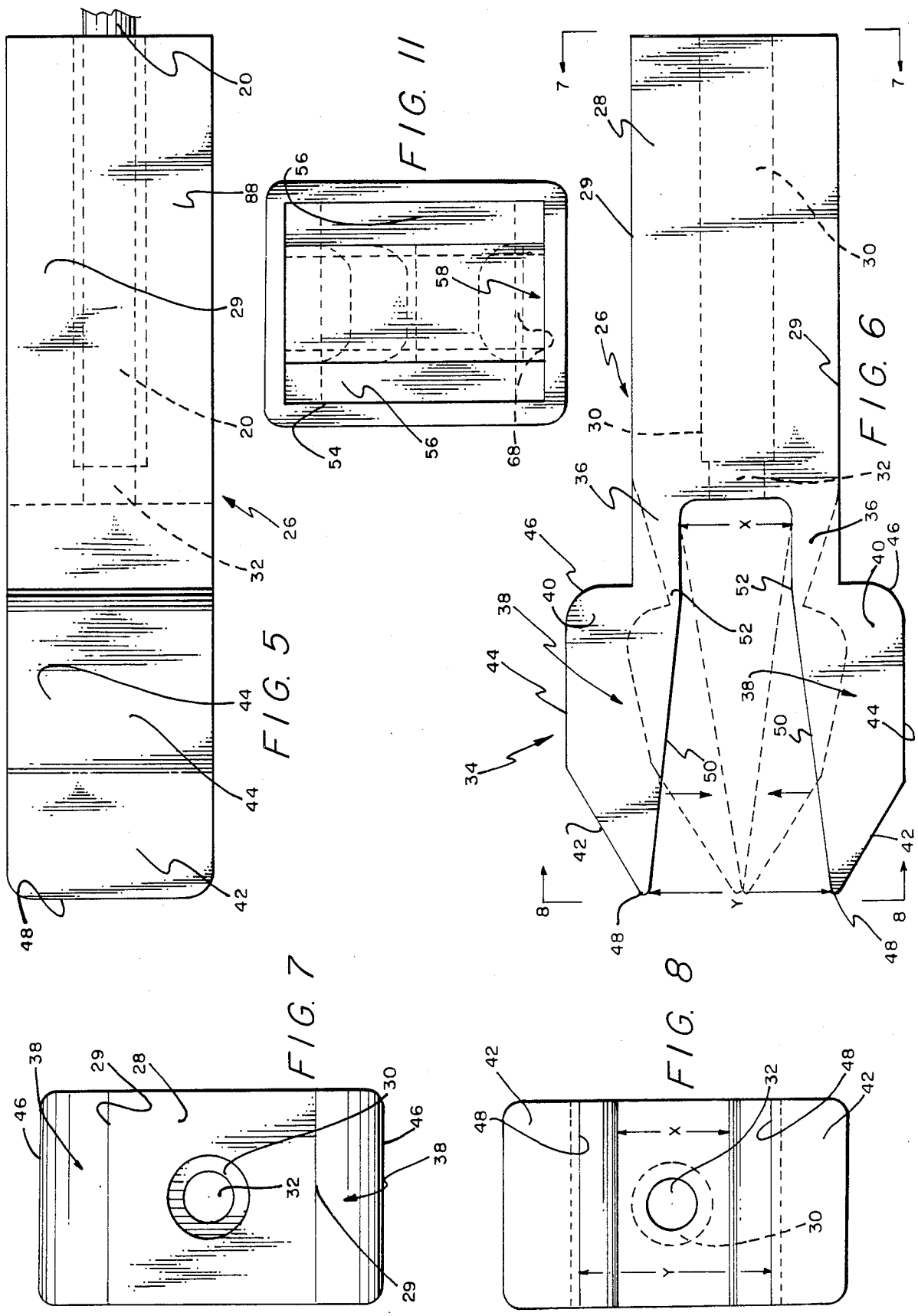

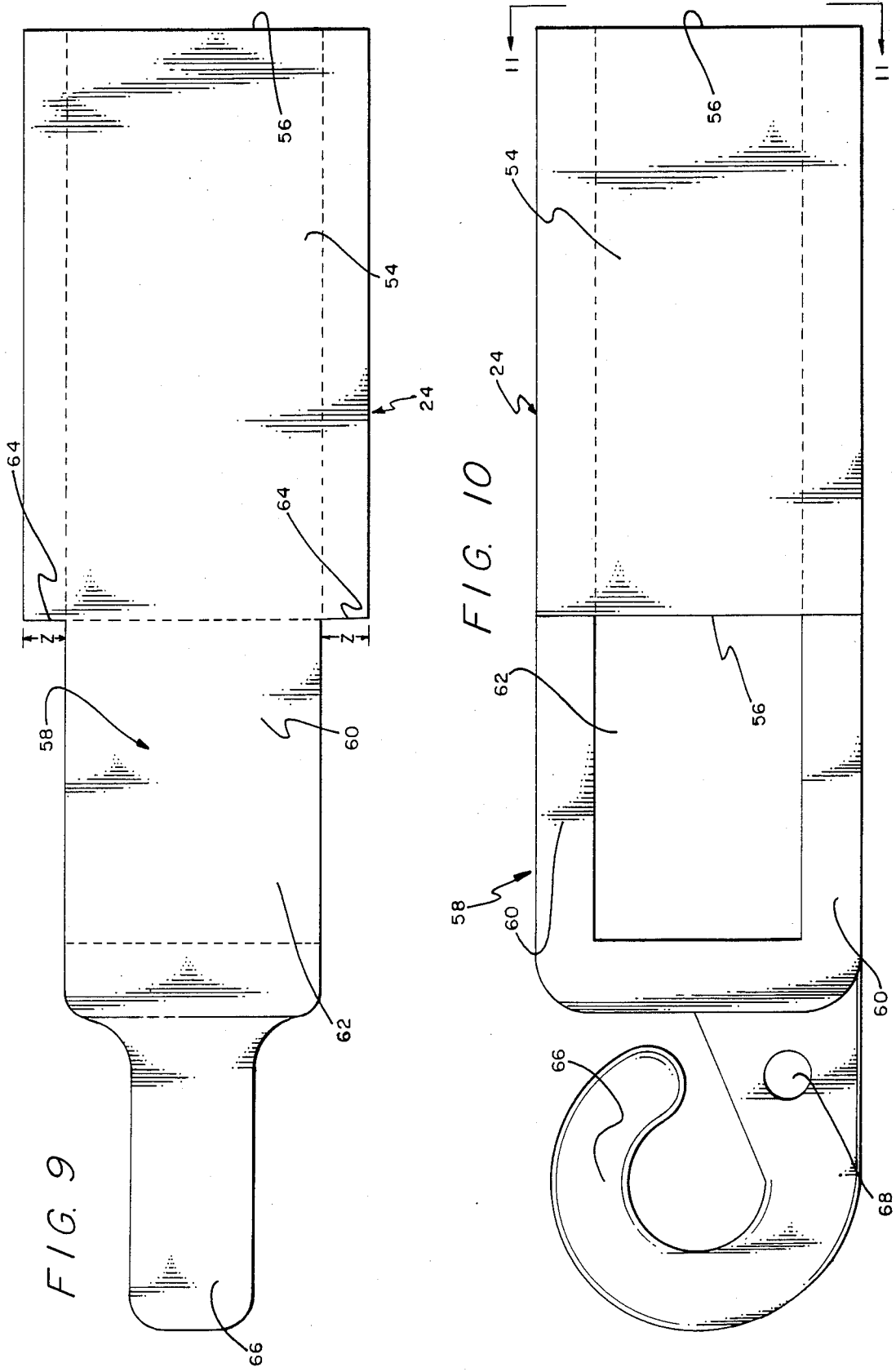

ORTHODONTIC HEADGEAR AND A METHOD FOR PREVENTING INJURIES TO PATIENTS UNDERGOING ORTHODONTIC TREATMENT WITH AN ORTHODONTIC HEADGEAR

BACKGROUND OF THE INVENTION

1. Field of the Invention

This invention is related to an orthodontic headgear. More specifically, this invention relates to an orthodontic headgear and a method for preventing injuries to patients undergoing orthodontic treatment with the orthodontic headgear.

2. Description of the Prior Art

Conventional orthodontic headgear consists of an inner bow which is mostly in the patient's mouth and is connected to braces on the patient's teeth; and an outer bow, which is fixed rigidly to the inner bow, is outside of the mouth and is used to apply pressure to the patient's teeth as a means of orthodontic correction. An elastic force from an elastic is applied to the ends of the outer bow through hooks bent into the ends of the outer bow. The elastic force originates from a skull cap or a neck pad that the patient wears.

Patients are instructed to remove the elastics before removing the bows. However, some patients do not follow instructions and attempt to remove the bows with the elastic attached. To do this, the patient must stretch the elastic. When the inner bow is finally pulled clear of the mouth, the elastic force from the elastic is very high. If the patient accidentally releases the bows, there is a possibility that the ends of the inner bow will puncture the eyes of the patient, causing permanent blindness.

There are several existing safety devices which consist of a release mechanism that is designed to disengage at a predetermined force. These existing devices limit the force that can be used for orthodontic treatment. If high forces are utilized, the release mechanism will disengage. If small forces are used, then it is still possible to remove the bows without triggering the release mechanism and the possibility of eye damage exist. Other existing systems use limiting straps which prevent the removal of the bows beyond a predetermined limit. This system can easily be by-passed by the patient by simply forgetting to add the limiting strap to the bows.

What is needed and what has been invented by me is an orthodontic headgear, and a method for preventing injuries to patients undergoing orthodontic treatment with the orthodontic headgear, which overcame the deficiencies of existing systems.

SUMMARY OF THE INVENTION

This invention broadly accomplishes its desired objects by providing an orthodontic headgear for preventing injuries to patients undergoing orthodontic treatment. The orthodontic headgear comprises an inner orthodontic bow means adapted to be secured to braces, and an outer orthodontic bow means integrally bound to the inner orthodontic bow means and formed with a pair of arms terminating into a pair of arm ends. A pair of safety hook means is connected stationarily to the pair of arm ends respectively. A safety line means is bound to each of the pair of safety hook means in order to limit the distance the outer bow can be displaced forward. The safety hooks means severs into a male member and a female member in the event there is force between the arm ends and the safety hook greater than about 9 lbs.

This invention also broadly accomplishes the desired objects by providing a method for preventing injuries to patients undergoing orthodontic treatment with an orthodontic headgear having an inner orthodontic bow means adapted to be secured to braces and an outer orthodontic bow means integrally bound to the inner orthodontic bow means and formed with a pair of arms terminating into a pair of arm ends. The method comprises the steps of binding respectively a pair of male members of a pair of safety hook means to the arm ends of the outer orthodontic bow means; attaching the ends of a safety line means to a pair of female members; and securing removably each male member to each female member in order to limit the distance the outer bow means and the inner bow means can be displaced forward to prevent the ends of the inner bow means from possibly puncturing the eyes of the patients, or other injuries.

Therefore, it is an object of the present invention to provide an orthodontic headgear and method for preventing injuries to patients undergoing orthodontic treatment.

It is another object of this invention to provide an orthodontic headgear, and a method for preventing injuries to patients undergoing orthodontic treatment, which limits the forward displacement of the face bow in order to protect the patient's eyes from a possible puncture from the sharp ends of the inner orthodontic bow.

These together with various ancillary objects and features which will become apparent to those skilled in the art as the following description proceeds, are attained by this orthodontic headgear and method for preventing injuries, a preferred embodiment being shown with reference to the accompanying drawings, by way of example only, wherein:

BRIEF DESCRIPTION OF THE DRAWINGS

FIG. 3 is a top plan view of the safety hook with the male member of the safety hook releasably engaged to the female member of the safety hook;

FIG. 4 is a side elevational view of the safety hook of FIG. 3;

FIG. 5 is a top plan view of the male member of the safety hook with an arm end of the outer orthodontic bow bound thereto;

FIG. 6 is a side elevational view of the male member of FIG. 5;

FIG. 7 is an end elevational view of the male member taken in direction of the arrows and along the plane of line 7—7 in FIG. 6;

FIG. 8 is an end elevational view of the male member taken in direction of the arrows and along the plane of line 8—8 in FIG. 6.

FIG. 9 is a top plan view of the female member of the safety hook;

FIG. 10 is a side elevational view of the female member of FIG. 9; and

FIG. 11 is an end elevational view of the female member taken in direction of the arrows and along the plane of line 11—11 in FIG. 10.

DETAILED DESCRIPTION OF THE INVENTION

Figure 1:
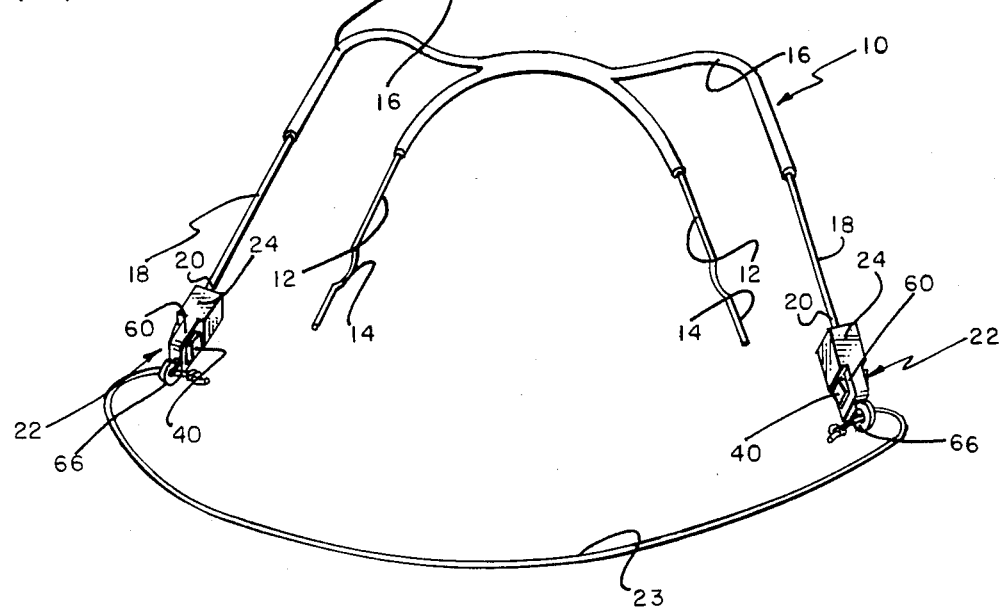
FIG. 1 is a perspective view of the orthodontic headgear of this invention with a safety line engaged.
Figure 2:
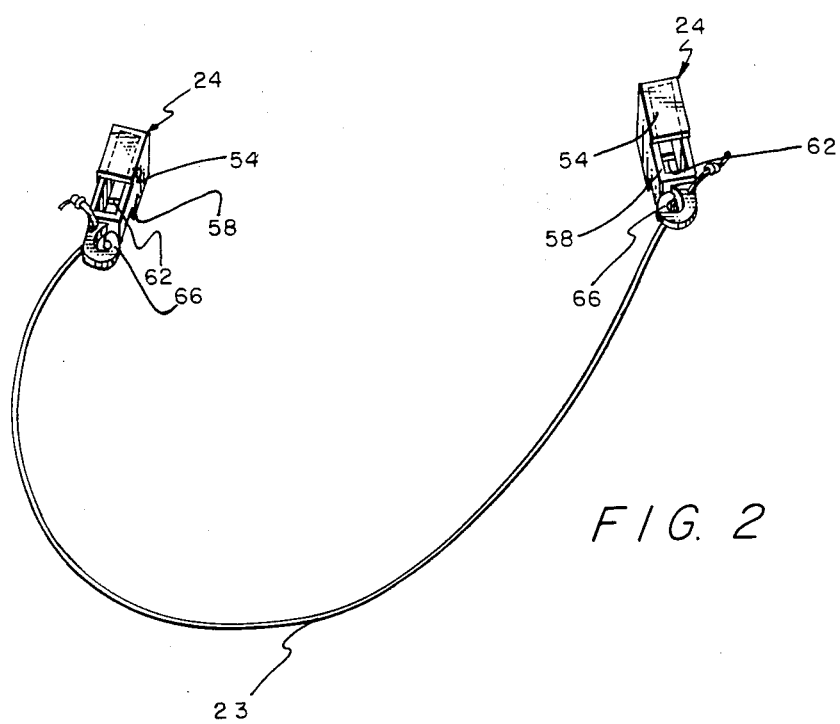
FIG. 2 is a perspective view of the safety line secured to female member of the safety hook of this invention.

Referring in detail now to the drawings for illustration of the novel orthodontic headgear, wherein like or similar parts of the novel orthodontic headgear are identified by like reference numerals, there is seen in general the orthodontic headgear of this invention, generally illustrated as 10, for preventing injuries to patients undergoing orthodontic treatment. The orthodontic headgear 10 includes an inner orthodontic bow 12 adapted to be secured to the patient's braces at 14, and an outer orthodontic bow 16 integrally bound to the inner orthodontic bow 12 and formed with a pair of arms 18—18 that terminate into a pair of arm ends, generally illustrated as 20—20. A pair of safety hooks, generally illustrated as 22—22, stationarily connected to the pair of arm ends 20—20, respectively. A safety line 23 is bound to each of the pair of safety hooks 22—22 in order to limit the distance the outer bow 16 can be displaced forward.

In a preferred embodiment of the invention, each safety hook 22 comprises a female member, generally illustrated as 24, and a male member, generally illustrated as 26. The female member 24 is releasably secured to the male member 26.

The male member 26 (see FIGS. 5-8) has a male body 28 with a body surface 29 and includes generally a cylindrical opening or recess 30. Cylindrical opening 30 terminates into another cylindrical opening 32 having a smaller diameter than cylindrical opening 30. An arm end 20 of an arm 18 of the outer orthodontic bow 16 is affixed within the cylindrical opening 30 (see FIG. 5) and is held therein by a binder such as cement, glue (e.g., superglue) or the like.

The male member 26 additionally has a resilient bifurcated fork means, general illustrated as 34 (see FIG. 6), integrally bound to the male body 28. The fork means 34 has a pair of fork ends 36—36. The fork arms 36—36 protrude from the male body 28 (as illustrated in FIG. 6) with a predetermined distance x separating the fork arms 36—36 at the location or point of where the arms 36—36 extend from the male body 28. Each of the fork arms 36—36 terminate into a fork end, generally illustrated as 38. Each fork end 38 has an outside flange 40 beginning in proximity to the male body 28 and terminating into a beveled flange end 42 at a point fartahest from the male body 28. Flange 40 has a flange surface 44 and an arcuate structure at 46. Flange surface 44 has an extremity point at 48. The extremity points 48—48 of the respective fork ends 38—38 or the respective flanges 40—40 are separated by a predetermined distance y separating the respective extremity points. Distance y is greater than distance x. An inside surface 50 of each of the fork ends 38—38 tapers away or outwardly from the inside of the two fork arms 36—36, commencing at 52 and ending at the extremity point 48. The fork arms 36—36 including their respective fork ends 38—38 are formed with a material (e.g., a polyethylene plastic or the like) to be resilient such as to be capable of being compressed in direction of the arrows to the dotted line position of FIG. 6. In this position, the flange surface 44 generally collimates with the body surface 29 of the male body 28.

Each female member 24 of the safety hook 22 has a female body 54 with a predetermined width (see FIG. 9) and open at both ends 56—56 for slidably, releasably receiving the pair of fork arms 36—36 of the male body 28 when the former are compressed into the dotted line position of FIG. 6. A generally U-shaped female end, generally illustrated as 58, is integrally bound to the female body 54. U-shaped female end 58 has a pair of female arms 60—60 and a pair of open sides 62—62. The U-shaped female end 58 also has a predetermined width which is less than the predetermined width of the female body 54 by a factor of 2z such as to form two ridges 64—64, with each ridge 64 having a height of z (see FIGS. 3 and 9). The height of the flanges 40—40 of the fork ends 38—38 is approximately the same height z of the ridges 64—64. After the compressed fork arms 36—36 have slidably passed all the way through the opening at ends 56—56, the compressed fork arms 36—36 snap back into their noncompressed position through the open sides 62—62 of U-shaped female end 58 such that the beginning of flanges 40—40 lodge against the ridges 64—64, as illustrated in FIG. 3, to releasably secure the male member 26 within the female member 24.

A hook 66 is integrally bound to the U-shaped female end 58 and operates to hold the elastic means (e.g., rubber bands, or the like) that is around the patient's head and places force on the patient's braces and teeth. Hook 66 has aperture 68 which receives an end of the safety line 23 which when positioned around a patient's head limits the distance the outer bow 16 and the inner bow 14 can be displaced forward away from the patient's face and prevents the possibility of the ends of the inner bow 12 puncturing the eyes of the patients. As an additional precaution in preventing injuries to patients from the ends of the inner bow 12, the safety hook 22 is manufactured such that the male member 26 is released from the female member 24 if the force between an arm end 20 (of arm 18 of outer bow 18) bound within the recess 30 of the male body 28 and an end of the safety line 23 (or the elastic means secured to hook 66) is greater than about 9 lbs. When any force between a male member 26 and a female member 24 occurs through arm 18 and safety line 23, such as by the patient pulling the outer bow 18 forward, the arm end 20 pulls the male member 26 forward while the safety line 23 (and/or the elastic means) retains the female member 24. The flanges 40—40 are forced against the ridges 64—64 which commences the compression of the fork ends 38—38 in direction of the arrows in FIG. 6. With continued force the fork ends 38—38 are compressed further until they reach the dotted line position of FIG. 6 where at the flange surfaces 44—44 and the arcuate structure at 46—46 register with the opening at ends 56—56. At the dotted line position of FIG. 6, the force between the male member 26 and the female member 24 is 9 lbs or greater, and the fork arms 36—36 have been unseated from the open sides 62—62 of U-shaped female end 58. The arcuate structures at 46—46 assist with the unseating (as well as the seating) of the flanges 40—40 with the ridges 64—64. Registration of the arcuate structures at 46—46 and the flange surfaces 44—44 allows the male member 24 to be slidably released from the female member 26 through the opening at the ends 56—56 of the female body 54. Now there is no danger of injury to the patient from the ends of the inner bow 12.

With the safety hook 22 of this invention, it is impossible for the patient to accidentally by-pass the safety feature of this invention since elastic force can not be imparted to the outer and inner bow 16 and 12 respectively without the safety hooks 22—22 being securely in place at the end of arm ends 20—20. The safety line means 23 protects the patient from possibly being punctured from the ends of inner bow 12. The safety hook means 22 also severs into the male member 26 and the female member 24 in the event there is force between the arms 18—18 of the outer bow 16 and the safety hook 22 greater than about 9 lbs. It should be understood that in the spirit and scope of this invention, there may be many ways to secure the arms ends 20—20 of the outer bow 16 to the male member 26 of the safety hooks 22—22 of this invention, which are interconnected by the safety line means 23. Any one or all of these possibly many ways to secure arm ends 20—20 to the male members 26—26 of the safety hooks 22—22 are within the scope of this invention.

While the present invention has been described herein with reference to particular embodiments thereof, a latitude of modification, various changes and substitutions are intended in the foregoing disclosure, and in some instances, some features of the invention will be employed without a corresponding use of other features without departing from the scope of the invention as set forth.

I claim:

1. An orthodontic headgear for preventing injuries to patients undergoing orthodontic treatment comprising an inner orthodontic bow means adapted to be secured to braces; an outer orthodontic bow means integrally bound to said inner orthodontic bow means and formed with a pair of arms terminating into a pair of arm ends; a pair of safety hook means connected stationarily respectively to said pair of arm ends; and safety line means bound to each of said pair of safety hooks means in order to limit the distance the outer bow can be displaced forward; each safety hook comprises a male member and a female member releasably secured to said male member; said male member comprises a male body having a structure defining a cylindrical recess that accommodates an arm end of the outer orthodontic bow means; said cylindrical recess extends through the entire male body to define generally a cylindrical opening; said male member additionally comprises a resilient bifurcated fork means integrally bound to said male body; said fork means comprises a pair of fork arms protruding from said male body with a first predetermined distance separating the fork arms at the point of where the fork arms protrude from the male body; each of said fork arms terminate into a fork end, each fork end has a structure defining an outside flange means that flanges outwardly at the closest point to the male body and terminates into a beveled flange end at a point farthest from the male body; each of said fork ends has a tapering inside surface that tapers outwardly and toward the flange means and terminates into the beveled flange end at a flange extremity point such that there is a second predetermined distance separating respective flange extremity point of respective fork ends, said second predetermined distance being greater than said first predetermined distance; said female member comprises a female body with a predetermined width and open at both ends for slidably, releasably receiving the pair of fork arms of said fork means; said female member additionally comprises a generally U-shaped female end means open to the atmosphere on opposed sides and having a pair of female arms with a predetermined width and integrally bound to the female body; said predetermined width of said female arms are less than said predetermined width of said female body; and said female member additionally comprises a hook integrally bound to the generally U-shaped female end, said hook has a structure defining an aperture for receiving a safety line.

2. The orthodontic headgear of claim 1 wherein said cylindrical opening that is defined by the cylindrical recess extending through the entire male body comprises a first cylindrical opening and a second cylindrical opening that is in direct communication with the first cylindrical opening.

3. The orthodontic headgear of claim 1 wherein said second cylindrical opening has a diameter that is less than the diameter of the first cylindrical opening.

4. The orthodontic headgear of claim 1 wherein said cylindrical opening is defined by the cylindrical recess extending through the entire male body comprises a first cylindrical opening and a second cylindrical opening that is in direct communication with the first cylindrical opening.

5. The orthodintic headgear of claim 4 wherein said second cylindrical opening has a diameter that is less than the diameter of the first cylindrical opening.

* * * * *